United States Patent
Grote et al.

(10) Patent No.: US 6,919,485 B2
(45) Date of Patent: Jul. 19, 2005

(54) BENZOPHENONES, THE PRODUCTION THEREOF AND THEIR USE FOR CONTROLLING PLANT PATHOGENIC FUNGI

(75) Inventors: Thomas Grote, Wachenheim (DE); Andreas Gypser, Mannheim (DE); Joachim Rheinheimer, Ludwigshafen (DE); Ingo Rose, Mannheim (DE); Peter Schäfer, Ottersheim (DE); Frank Schieweck, Hessheim (DE); Norbert Götz, Worms (DE); Karl Eicken, Wachenheim (DE); Eberhard Ammermann, Heppenheim (DE); Siegfried Strathmann, Limburgerhof (DE); Gisela Lorenz, Hambach (DE); Reinhard Stierl, Mutterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/469,688

(22) PCT Filed: Mar. 9, 2002

(86) PCT No.: PCT/EP02/02612

§ 371 (c)(1),
(2), (4) Date: Sep. 3, 2003

(87) PCT Pub. No.: WO02/072523

PCT Pub. Date: Sep. 19, 2002

(65) Prior Publication Data

US 2004/0082815 A1 Apr. 29, 2004

(30) Foreign Application Priority Data

Mar. 13, 2001 (DE) .......................................... 101 12 876

(51) Int. Cl.⁷ .......................... C07C 45/00; A01N 35/00

(52) U.S. Cl. ........................ 568/312; 568/314; 568/316; 568/319; 568/332; 504/348; 504/352

(58) Field of Search .................................. 568/312, 314, 568/316, 319, 332; 504/348, 352

(56) References Cited

U.S. PATENT DOCUMENTS 5,922,919 A * 7/1999 Curtze et al. ................ 568/322
5,945,567 A * 8/1999 Curtze et al. ................ 568/333

FOREIGN PATENT DOCUMENTS

EP  727 141  8/1996
EP  899 255  3/1999

* cited by examiner

Primary Examiner—James O. Wilson
Assistant Examiner—Sikarl A. Witherspoon
(74) Attorney, Agent, or Firm—Novak Druce & Quigg

(57) ABSTRACT

The invention relates to benzophenones of formula (I), in which the substituents have the following meanings: X represents halogen; $R^1$ represents hydrogen, halogen, $C_1$–$C_6$ alkyl, halo-$C_1$–$C_2$ alkyl, $C_1$–$C_4$ alkoxy, oxyhalomethyl or nitro, and; $R^2$ represents hydrogen, $C_1$–$C_6$ alkyl, benzyl, cyclohexylmethyl or $C_3$–$C_6$ alkenyl. The invention also relates to the production of these benzophenones and to their use as fungicides

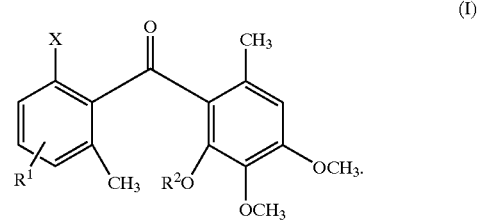

(I)

11 Claims, No Drawings

BENZOPHENONES, THE PRODUCTION THEREOF AND THEIR USE FOR CONTROLLING PLANT PATHOGENIC FUNGI

The invention relates to benzophenones of the formula I

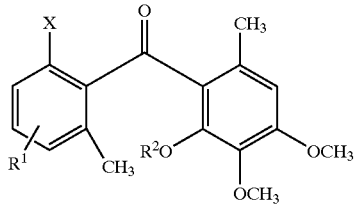

in which the substituents have the following meanings:
X is halogen;
$R^1$ is hydrogen, halogen, $C_1$–$C_6$-alkyl, halo-$C_1$–$C_2$-alkyl, $C_1$–$C_6$-alkoxy, oxyhalomethyl or nitro;
$R^2$ is hydrogen, $C_1$–$C_6$-alkyl, benzyl, cyclohexylmethyl or $C_3$–$C_6$-alkenyl.

The invention furthermore relates to a process for the preparation of the compounds of the formula I, to compositions for controlling phytopathogenic fungi comprising the compounds I, and to the use of the compounds I for controlling phytopathogenic fungi.

The compound 2-chloro-2',6-dimethyl-4',5'-dimethoxybenzophenone and its use as fungicide are disclosed in EP-A 727141. However, the compound does not meet all the requirements which fungicidal active ingredients must meet in practice.

It is an object of the present invention to provide compounds with an improved action and/or widened spectrum of action.

We have now found that this object is achieved by compounds which have the substitution patterns according to the invention: one of the two phenyl radicals of the benzophenone has a halogen atom attached in the 2-position and a methyl group in the 6-position, while the other phenyl moiety of the benzophenone constitutes a 4',5',6'-trialkoxy-2-tolyl radical.

The abovementioned meanings constitute collective terms for individual enumerations of individual group members. All of the carbon chains can be straight-chained or branched. Halogenated substituents preferably have 1 to 5 identical or different halogen atoms attached to them.

Examples of individual meanings are:
halogen: fluorine, chlorine, bromine, iodine, preferably chlorine or bromine;
$C_1$–$C_6$-alkyl in particular $C_1$–$C_4$-alkyl: methyl, ethyl, n-propyl, 1-methylethyl, n-butyl, 1-methylpropyl, 2-methylpropyl, 1,1-dimethylethyl, preferably methyl;
halo-$C_1$–$C_2$-alkyl: a methyl or ethyl group having 1 to 3 halogen atoms;
$C_1$–$C_4$-alkoxy: methoxy, ethoxy, n-propoxy, 1-methylethoxy, n-butoxy, 1-methylpropoxy, 2-methylpropoxy, 1,1-dimethylethoxy, preferably methoxy;
oxyhalomethyl: a methoxy group which has 1 to 3 halogen atoms attached to the methyl moiety;
$C_3$–$C_6$-alkenyl: prop-1-en-1-yl, prop-2-en-1-yl, 1-methylethenyl, buten-1-yl, buten-2-yl, buten-3-yl, 1-methylprop-1en-1-yl, 2-methylprop-1-en-1-yl, 1-methylprop-2-en-1-yl and 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, hex-1-en-1-yl,
hex-2-en-1-yl, hex-3-en-1-yl, hex-4-en-1-yl, hex-5-en-1-yl,
1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl or 1-ethyl-2-methylprop-2-en-1-yl.

In view of their fungicidal action, the following substituents are preferred, the preference being given in each case alone or in combination:

Preferred are benzophenones of the formula Ia in which the substituent $R^1$ is in the 5-position.

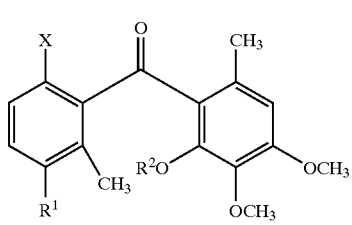

Particularly preferred are benzophenones of the formula I or Ia where $R^1$ is hydrogen, fluorine, chlorine or bromine.

Furthermore preferred are benzophenones of the formula I or Ia where X is fluorine, chlorine or bromine.

Preferred benzophenones are, moreover, those of the formula I or Ia where $R^2$ is methyl.

Examples of particularly preferred benzophenones are compiled in the tables which follow.

TABLE 1

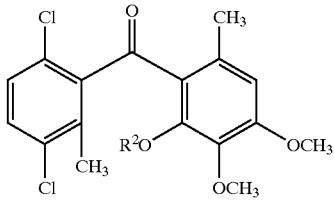

Benzophenones I.1–01 to I.1–14 of the formula I.1

| Number | $R^2$ |
|---|---|
| 1. | H |
| 2. | $CH_3$ |
| 3. | $n-C_3H_7$ |
| 4. | $i-C_3H_7$ |
| 5. | $n-C_4H_9$ |
| 6. | $s-C_4H_9$ |
| 7. | $t-C_4H_9$ |
| 8. | $n-C_5H_{11}$ |
| 9. | $s-C_5H_{11}$ |
| 10. | $t-C_5H_{11}$ |
| 11. | $n-C_6H_{13}$ |
| 12. | $CH_2-C_6H_5$ |
| 13. | cyclohexylmethyl |
| 14. | $CH_2CH=CH$ |

TABLE 2

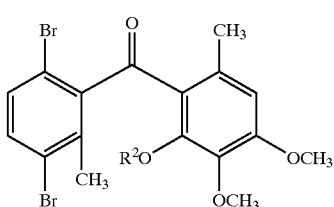

Benzophenones I.2-01 to I.2-14 of the formula I.2, in which the meaning of $R^2$ is shown by the rows of table 1.

TABLE 3

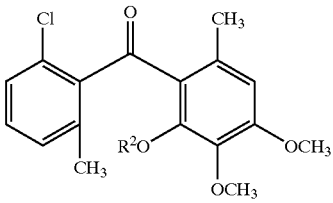

Benzophenones I.3-01 to I.3-14 of the formula I.3, in which the meaning of $R^2$ is shown by the rows of table 1.

TABLE 4

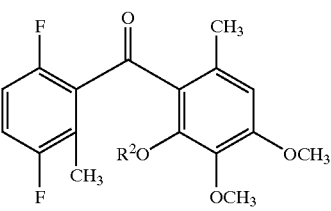

Benzophenones I.4-01 to I.4-14 of the formula I.4, in which the meaning of $R^2$ is shown by the rows of table 1.

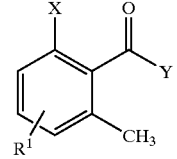

Benzophenones I.5-01 to I.5-14 of the formula I.5, in which the meaning of $R^2$ is shown by the rows of table 1.

The novel compounds I are synthesized by coupling a 2-halo-6-methylbenzoic acid derivative of the formula II (IIa or IIb)

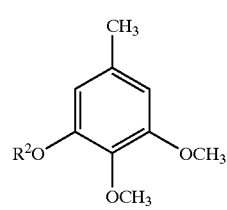

IIa: y = OH
IIb: y = halogen in which the substituents X and $R^1$ have the meanings stated in claim 1 with a tolyl derivative of the formula III in which $R^2$ has the meaning stated in claim 1 in the presence of a catalyst.

If the coupling step is carried out with the free carboxylic acid IIa (Y=OH), the catalyst employed is, as a rule, a dehydrating agent such as phosphorus pentoxide or phosphorus oxychloride. In the first case, reaction temperatures of from 0 to 50° C. and, in particular, room temperature are recommended, in the latter case, higher temperatures of from 50 to 180° C. are generally necessary.

In an equally preferred, alternative process, the carboxylic acids IIa can first be converted into the corresponding acid halides IIb (Y=halogen) and only then be coupled to the tolyl derivative III. The reaction of the carboxylic acids IIa to give the acid halides IIb is carried out with chlorinating or brominating agents such as phosphorus oxybromide, phosphorus oxychloride, thionyl chloride, thionyl bromide or sulfuryl chloride, following standard methods (see, for example, Organikum [Organic Chemistry], 19th Edition, Edition Deutscher verlag der Wissenschaften, p. 440).

As a rule, the acid halides IIb are coupled to the tolyl derivatives III in the presence of catalysts. Catalysts which have proved suitable are Lewis acids such as aluminum chloride, tin chloride, zinc chloride, titanium tetrachloride, antimony pentachloride or boron trifluoride, or acidic ion-exchanger resins such as Amberlyst™15 or Nafion™. Particularly suitable as catalyst is iron(III) chloride. This is usually employed in concentrations of from 0.001 to 0.2 molar equivalents at temperatures of from 50 to 180° C. The coupling reaction can be carried out in the presence of an inert organic solvent.

The starting materials II and III can be obtained by processes known from the literature.

With reference to 2,5-dichloro-6-methylbenzoic acid (II.a1), a synthesis route disclosed in WO-A 00/29395 which gives the carboxylic acids IIa is shown in scheme 1. Here, a benzyl bromide is oxidized with N-methylmorpholine N-oxide (NMMO) to give the aldehyde, which can be oxidized further by standard methods (for example *J.Chem.Soc., Perkin Trans.* I, 947 (1986)) to give the benzoic acid derivative.

Scheme 1:

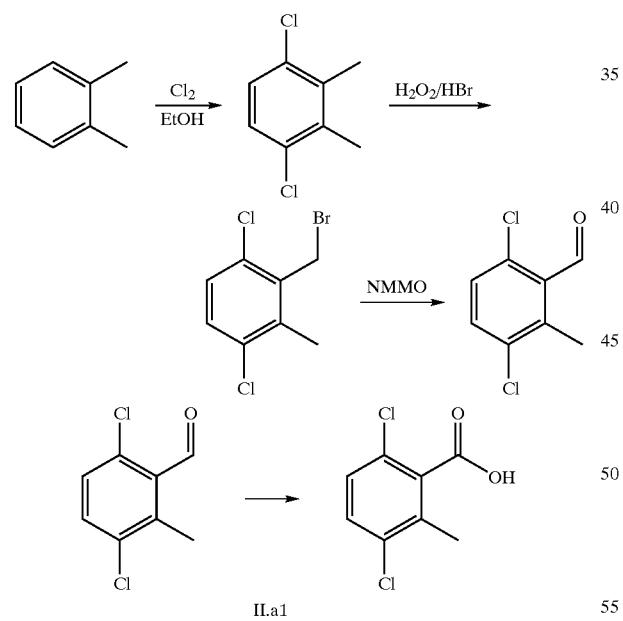

As an alternative to the route shown above, the type IIa compounds can be obtained by directly oxidizing the methyl function to give the carboxyl function, for example in accordance with *J. Org. Chem.* 1997, 62, 6810–13 using atmospheric oxygen, cobalt(II) acetate and N-hydroxyphthalimide or by oxidation with atmospheric oxygen in the presence of manganese(II) acetate.

For example, 3,6-difluoro-2-methylbenzoic acid (II.a2) is prepared as shown in scheme 2.

Scheme 2:

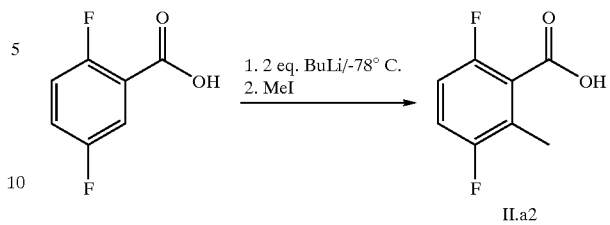

The further reaction of the carboxylic acids II.a1 and II.a2 with 3,4,5-trimethoxytoluene to give the active ingredients I.1-02 and I.5-02 is preferably carried out in the presence of phosphorus pentoxide (see synthesis examples 1 and 2).

The tolyl derivatives of the formula III can be obtained via the routes described in EP-A 897904 and EP-A 899255.

The novel compounds I are distinguished by an outstanding activity against a broad spectrum of phytopathogenic fungi, in particular from the classes of the Ascomycetes and Basidiomycetes, and can be employed as foliar- and soil-acting fungicides. Some of them are systemically translocated remarkably well and are remarkably active following soil application and in particular following foliar application.

They are of special importance for controlling a large number of fungi on various crop plants such as wheat, rye, barley, oats, rice, maize, grass, bananas, cotton, soybeans, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases:

Alternaria species in vegetables and fruit,
*Botrytis cinerea* (gray mold) in strawberries, vegetables, ornamentals and grapevines,
*Cercospora arachidicola* in peanuts,
*Erysiphe cichoracearum* and *Sphaerotheca fuliginea* in cucurbits,
*Erysiphe graminis* (powdery mildew) in cereals,
*Fusarium* and *Verticillium* species in a variety of plants,
*Helminthosporium* species in cereals,
*Mycosphaerella* species in bananas and peanuts,
*Phytophthora infestans* in potatoes and tomatoes,
*Plasmopara viticola* in grapevines,
*Podosphaera leucotricha* in apples,
*Pseudocercosporella herpotrichoides* in wheat and barley,
*Pseudoperonospora* species in hops and cucumbers,
*Puccinia* species in cereals,
*Pyricularia oryzae* in rice,
*Rhizoctonia* species in cotton, rice and lawns,
*Septoria nodorum* in wheat,
*Sphaerotheca fuliginea* (powdery mildew of cucumber) in cucumbers,
*Uncinula necator* in grapevines,
*Ustilago* species in cereals and sugar cane, and
*Venturia* species (scab) in apples and pears.

The compounds I are also suitable for controlling harmful fungi such as *Paecilomyces variotii* in the protection of materials (for example timber, paper, paint dispersions, fibers or tissue) and in the protection of stored products.

The compounds I are applied by treating the fungi or the plants, seeds or materials to be protected from fungal infection, or the soil, with a fungicidally active amount of the active ingredients. Application can be effected both before and after infection of the materials, plants or seeds by the fungi.

In general, the fungicidal compositions comprise between 0.1 and 95, preferably between 0.5 and 90%, by weight of active ingredient.

When used in the protection of plants, the application rates are between 0.01 and 2.0 kg of active ingredient per ha, depending on the nature of the desired effect.

In the treatment of seeds, amounts of active ingredient of from 0.001 to 0.1 g, preferably from 0.01 to 0.05 g, are generally required per kilogram of seeds.

When used in the protection of materials or stored products, the application rate of active ingredient depends on the nature of the field of application and the desired effect. Customary application rates in the protection of materials are, for example, from 0.001 g to 2 kg, preferably from 0.005 g to 1 kg, of active ingredient per cubic meter of material treated.

The compounds I can be converted into the customary formulations, for example solutions, emulsions, suspensions, dusts, powders, pastes and granules. The use form depends on the intended purpose in each case; in any case, it should ensure fine and uniform distribution of the compound according to the invention.

The formulations are prepared in a customary fashion, for example by extending the active ingredient with solvents and/or carriers, if appropriate using emulsifiers and dispersants, it also being possible to use other organic solvents as cosolvents if water is used as the diluent. Auxiliaries which can be used for this purpose are essentially: solvents such as aromatics (for example xylene), chlorinated aromatics (for example chlorobenzenes), paraffins (for example mineral oil fractions), alcohols (for example methanol, butanol), ketones (for example cyclohexanone), amines (for example ethanolamine, dimethylformamide) and water; carriers such as natural ground minerals (for example kaolins, clays, talc, chalk) and ground synthetic minerals (for example highly-dispersed silica, silicates); emulsifiers such as nonionic and anionic emulsifiers (for example polyoxyethylene fatty alcohol ether, alkylsulfonates and arylsulfonates) and dispersants such as lignin-sulfite waste liquors and methylcellulose.

Suitable surface-active substances are alkali metal salts, alkaline earth metal salts and ammonium salts of lignosulfonic acid, of naphthalenesulfonic acid, of phenolsulfonic acid, of dibutylnaphthalenesulfonic acid, alkylarylsulfonates, alkyl sulfates, alkylsulfonates, fatty alcohol sulfates and fatty acids, and their alkali metal and alkaline earth metal salts, salts of sulfated fatty alcohol glycol ether, condensates of sulfonated naphthalene and naphthalene derivatives with formaldehyde, condensates of naphthalene or naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, alkylaryl polyether alcohols, isotridecyl alcohol, fatty alcohol/ ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Materials which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, for example dimethylformamide, dimethyl sulfoxide, N-methylpyrrolidone or water.

Powders, materials for spreading and dusts can be prepared by mixing or concomitantly grinding the active substances together with a solid carrier.

Granules, for example coated granules, impregnated granules and homogeneous granules, can be prepared by binding the active ingredients to solid carriers. Examples of solid carriers are mineral earths such as silica gel, silicic acids, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers such as, for example, ammonium sulfate, ammonium phosphate, ammonium nitrate, ureas and products of vegetable origin, such as cereal meal, tree bark meal, wood meal and nutshell meal, cellulose powders and other solid carriers.

In general, the formulations comprise between 0.01 and 95% by weight, preferably between 0.1 and 90% by weight, of the active ingredient. The active ingredients are employed in a purity of from 90% to 100%, preferably 95% to 100% (according to NMR spectrum).

Examples of formulations are:

I. 5 parts by weight of a compound according to the invention are mixed intimately with 95 parts by weight of finely divided kaolin. This gives a dust comprising 5% by weight of the active ingredient.

II. 30 parts by weight of a compound according to the invention are mixed intimately with a mixture of 92 parts by weight of pulverulent silica gel and 8 parts by weight of paraffin oil with which the surface of this silica gel has been sprayed. This gives a preparation of the active ingredient with good adhesion (active ingredient content 23% by weight).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (active ingredient content 9% by weight).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (active ingredient content 16% by weight).

V. 80 parts by weight of a compound according to the invention are mixed thoroughly with 3 parts by weight of sodium diisobutylnaphthalene-α-sulfonate, 10 parts by weight of the sodium salt of a lignosulfonic acid from a sulfite waste liquor and 7 parts by weight of pulverulent silica gel, and the mixture is ground in a hammer mill (active ingredient content 80% by weight).

VI. 90 parts by weight of a compound according to the invention are mixed with 10 parts by weight of N-methyl-α-pyrrolidone, which gives a solution which is suitable for use in the form of microdrops (active ingredient content 90% by weight).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethyleneoxide and 1 mol of castor oil. Pouring the solution into 100 000 parts by weight of water and finely distributing it therein gives an aqueous dispersion comprising 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20 000 parts by weight of water gives a spray mixture comprising 0.1% by weight of the active ingredient.

IX. 10 parts by weight of the compound according to the invention are dissolved in 63 parts by weight of cyclohexanone, 27 parts by weight of dispersant (for example a mixture of 50 parts by weight of the adduct of 7 mol of ethylene oxide and 1 mol of isooctylphenol and 50 parts by weight of the adduct of 40 mol of ethylene oxide and 1 mol of castor oil). The stock solution is subsequently diluted by distributing in water to the desired concentration, for example to a concentration in the range of from 1 to 100 ppm.

The active ingredients can be used as such, in the form of their formulations or the use forms prepared therefrom, for example in the form of directly sprayable solutions, powders, suspensions or dispersions, emulsions, oil dispersions, pastes, dusts, materials for spreading, granules, by means of spraying, atomizing, dusting, spreading or pouring. The use forms depend entirely on the intended uses; in any case, they should guarantee the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of wetters, adhesives, dispersants or emulsifiers. However, it is also possible to prepare concentrates composed of active substance, wetter, adhesive, dispersant or emulsifier and, if appropriate, solvent or oil, and such concentrates are suitable for dilution with water.

The active ingredient concentrations in the ready-to-use preparations can be varied within substantial ranges. In general, they are between 0.0001 and 10%. Frequently, low application rates of compound I in the ready-to-use preparation frequently suffice, for example from 2 to 200 ppm. Ready-to-use preparations with active ingredient concentrations in the range of from 0.01 to 1% are likewise preferred.

Also, the active ingredients can be used very successfully in the ultra-low-volume method (ULV), it being possible to apply formulations with over 95% by weight of active ingredient, or even the active ingredient without additions.

Various types of oils, orherbicides, fungicides, other pesticides, bactericides, may be added to the active ingredients, if appropriate also only immediately prior to use (tank mix). These agents can be admixed with the agents according to the invention in a weight ratio of 1:10 to 10:1.

In the use form as fungicides, the agents according to the invention may also be present together with other active ingredients, for example with herbicides, insecticides, growth regulators, fungicides, or else with fertilizers. Mixing the compounds I or the compositions comprising them in their use form as fungicides with other fungicides frequently results in a broadened fungicidal spectrum of action.

The following list of fungicides together with which the compounds according to the invention can be used is intended to illustrate the possible combinations, but not to impose any limitation:

sulfur, dithiocarbamates and their derivatives, such as iron(III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl)disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenylisopropyl carbonate, diisopropyl 5-nitro-isophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonylaminobenzimidazole, 2-(2-furyl) benzimidazole, 2-(4-thiazolyl)benzimidazole, N-(1,1,2,2-tetrachloroethylthio)tetrahydrophthalimide, N-trichloromethylthiotetrahydrophthalimide, N-trichloromethylthiophthalimide;

N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol 1-oxide, 8-hydroxyquinoline or its copper salt, 2,3-dihydro-5-carboxanilido-6-methyl-1,4-oxathiine, 2,3-dihydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis-1-(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol1-yl)-2-butanone, 1-(4-chlorophenoxy)-3,3-dimethyl1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-t α-(2-chlorophenyl)-α-(4-chlorophenyl)-5- pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene;

strobilurins such as methyl E-methoxyimino-[α-(o-tolyloxy)-o-tolyl]acetate, methyl E-2-{2-[6-(2-cyanophenoxy)pyrimidin-4-yloxy]phenyl}-3-methoxyacrylate, N-methyl-E-methoxyimino-[α-(2-phenoxyphenyl)]acetamide, N-methyl-E-methoxyimino-[α-(2,5-dimethylphenoxy)-o-tolyl]acetamide, methyl E-2-{2-[(2-trifluoromethylpyridyl-6-)oxymethyl]phenyl}-3-methoxyacrylate, methyl (E,E)-methoximino-{2-[1-(3trifluoromethylphenyl) ethylideneaminooxymethyl]phenyl} acetate, methyl N-(2-{[1-(4-chlorophenyl)-1H-pyrazol-3yl] oxymethyl}phenyl)-N-methoxycarbamate, anilinopyrimidines such as N-(4,6-dimethylpyrimidin-2-yl)aniline, N-[4-methyl-6-(1-propynyl)pyrimidin-2-yl] aniline, N-[4-methyl-6-cyclopropylpyrimidin-2-yl] aniline;

phenylpyrroles such as 4-(2,2-difluoro-1,3-benzodioxol-4yl)pyrrole-3-carbonitrile;

cinnamamides such as 3-(4-chlorophenyl)-3-(3,4-dimethoxyphenyl)acryloylmorpholine;

and a variety of fungicides such as dodecylguanidine acetate, 3-[3-(3,5-dimethyl-2-oxycyclohexyl)-2-hydroxyethyl]glutarimide, hexachlorobenzene, methyl N-(2,6-dimethylphenyl)N-(2-furoyl)-DL-alaninate, DL-N-(2,6-dimethylphenyl)-N-(2'-methoxyacetyl) alanine methyl ester, N-(2,6-dimethylphenyl)-N-chloroacetyl-D,L-2-aminobutyrolactone, DL-N-(2,6-dimethylphenyl)-N-(phenylacetyl)alanine methyl ester, 5-methyl-5-vinyl-3-(3,5-dichlorophenyl)-2,4-dioxo-1,3-oxazolidine, 3-[3,5-dichlorophenyl-(5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2dicarboximide, 2-cyano-[N-(ethylaminocarbonyl)2-methoximino]acetamide, 1-[2-(2,4-dichlorophenyl) pentyl]-1H-1,2,4-triazole, 2,4-difluoro-α-(1H-1,2,4-triazolyl-1-methyl)benzhydryl alcohol, N-(3-chloro-2,6-dinitro-4-trifluoromethylphenyl)-5-trifluoromethyl-3-chloro-2-aminopyridine, 1-((bis(4-fluorophenyl) methylsilyl)methyl)-1H-1,2,4-triazole.

The invention will now be illustrated in greater detail with reference to the use examples which follow.

SYNTHESIS EXAMPLES

Example 1

2,5-Dichloro-2',6-dimethyl-4',5',6'-trimethoxybenzophenone (I.1-02)

14 g (68.29 mmol) of 2,5-dichloro-6-methylbenzoic acid were introduced into 1000 ml of dichloromethane. 11.2 g (61.6 mmol) of 3,4,5-trimethoxytoluene and 28 g of finely ground phosphorus pentoxide were added. After 2 hours of stirring at room temperature, the reaction solution, which by now was orangey red, was poured into water and extracted three times with dichloromethane. The combined organic phases were washed twice with water, dried with sodium sulfate and concentrated, and the reaction product was then isolated by column chromatography using a methyl tert-butyl ether/hexane gradient. This gave 20.1 g of the title compound (yield 80%).

Example 2

2,5-Difluoro-2',6-dimethyl-4',5',6'-trimethoxybenzophenone (I.5-02)

Stage 1: 3,6-Difluoro-2-methylbenzoic acid 10 g (0.063 mol) of 2,5-difluorobenzoic acid were introduced into 100 ml of dry THF under a nitrogen atmosphere. 99 ml (0.158 mol) of a 1.6-molar butyl lithium solution in hexane were added dropwise at −74° C. in the course of 30 minutes. After stirring had been continued for 20 minutes at −74° C., 18.0 g (0.127 mol) of methyl iodide were added dropwise. The reaction mixture was heated to room temperature, 50 ml of 5% strength HCl were added, and the organic phase was separated off, washed once with water and dried over magnesium sulfate. This gave 8.4 g of a solid which was extracted by stirring with 80 ml of cyclohexane, filtered off with suction, washed with a little cyclohexane and dried. This gave 5.9 g of 3,6-difluoro-2-methylbenzoic acid of 95% purity (Yield: 51% of theory).

$^1$H NMR (CDCl$_3$): 2.3 ppm (s; 3 H; CH$_3$), 7.2 ppm (m, 1 H; arom. H); 7.3 ppm (m; 1 H; arom. H). $^{13}$C NMR (CDCl$_3$): 11.7 ppm (s, C-8); 114.5 ppm (d, C-5); 117.5 ppm (d, C-4); 123.9 ppm (s, C-1); 124.6 ppm (s, C-1); 154.5 ppm (d, C-3); 156.7 ppm (d, C-6); 165.6 ppm (s, COOH).

Stage 2:

9.3 g (54.3 mmol) of 3,6-difluoro-2-methylbenzoic acid and 9.88 g (54.3 mmol) of 3,4,5-trimethoxytoluene were introduced into 250 ml of absolute dichloromethane, and 54 g (380 mmol) of pulverulent phosphorus pentoxide were then added. The mixture was stirred for 16 hours at room temperature. According to HPLC check, the trimethoxytoluene had not been reacted completely. A further 13.5 g of phosphorus pentoxide were added. After a further four hours, the reaction mixture was poured into water and extracted with dichloromethane. The combined organic phases were then dried and concentrated. The crude product was purified by reversed-phase MPLC (eluent acetonitrile/water 7:3). This gave 12.2 g of the compound I.5-02 (36 mmol, 67% yield).

Use Examples

The fungicidal action of the compounds of the formula I is demonstrated by the following experiments.

The active ingredients, separately or jointly, were prepared as a 10% strength emulsion in a mixture of 70% by weight of cyclohexanone, 20% by weight of Nekanil® LN (Lutensol® AP6, wetter with emulsifying and dispersing action based on ethoxylated alkylphenols) and 10% by weight of Wettol® EM (nonionic emulsifier based on ethoxylated castor oil) and diluted with water to give the desired concentration.

Use Example 1—Activity Against Powdery Mildew of Wheat (*Erysiphe graminis* f. sp. *hordei* f. sp. *tritici*)

Leaves of wheat seedlings cv. "Kanzler" which have grown in pots were sprayed to runoff point with aqueous preparation of active ingredient made with a stock solution composed of 10% of active ingredient, 63% of cyclohexanone and 27% of emulsifier, and, 24 hours after the spray coating had dried on, dusted with spores of powdery mildew of wheat (*Erysiphe graminis* forma specialis *tritici*). The test plants were subsequently placed in a greenhouse at temperatures between 20 and 24° C. and a relative atmospheric humidity of 60 to 90%. After 7 days, the extent of the mildew development was determined visually in % disease of the total leaf area.

In one experiment, the plants treated with 16 ppm of the compounds I.1-02 and I.5-02 according to the invention showed no disease, while the untreated plants showed a disease level of 90%.

In a corresponding experiment, the plants treated with 4 ppm of the compound I.1-02 according to the invention showed no disease, the plants treated with 4 ppm of the compound I.5-02 showed a disease level of 1%, while the untreated plants showed a disease level of 90%.

We claim:
1. A benzophenone of the formula I

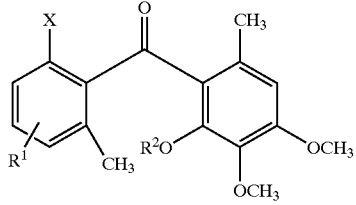

I in which the substituents have the following meanings:

X is halogen;

$R^1$ is hydrogen, fluorine, chlorine or bromine;

$R^2$ is methyl.

2. A benzophenone of the formula Ia

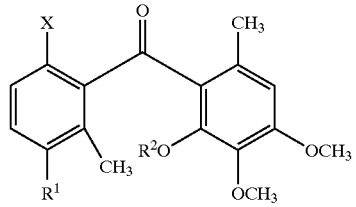

Ia in which the substituents X, $R^1$ and $R^2$ have the meanings stated in claim 1.

3. A process for the preparation of the compounds I as claimed in claim 1, wherein a 2-halo-6-methylbenzoic acid derivative of the formula II (IIa or IIb)

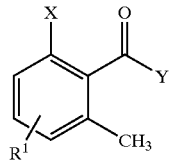

IIa: y = OH
IIb: y = halogen in which the substituents X and $R^1$ have the meanings stated in claim 1, is reacted with a tolyl derivative of the formula III

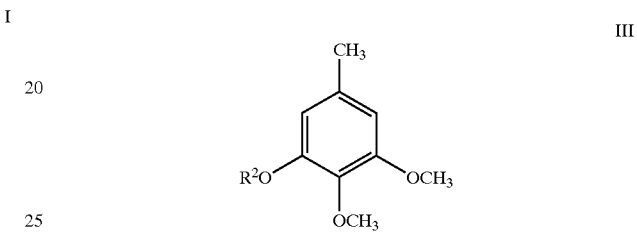

III in which the substituents $R^2$ has the meanings stated in claim 1, in the presence of a catalyst.

4. A fungicidal composition comprising solid and/or liquid carriers and a fungicidally active amount of at least one compound of the formula I as claimed in claim 1.

5. A method of controlling phytopathogenic fungi, where the fungi or the materials, plants or seeds at risk from fungal infection, or the soil, are treated with a fungicidally active amount of at least one compound of the formula I as claimed in claim 1.

6. The benzophenone of claim 2, wherein X and $R^1$ are chlorine.

7. The benzophenone or claim 2, wherein X and $R^1$ are bromine.

8. The benzophenone of claim 2, wherein X is bromine and $R^1$ is hydrogen.

9. The benzophenone of claim 2, wherein X is chlorine and $R^1$ is hydrogen.

10. The benzophenone of claim 2, wherein X and $R^1$ are fluorine.

11. The method of claim 5, wherein the fungi are from the class Ascomycetes or Basidiomycetes.

* * * * *

UNITED STATES PATENT AND TRADEMARK OFFICE
CERTIFICATE OF CORRECTION

PATENT NO. : 6,919,485 B2
DATED : July 19, 2005
INVENTOR(S) : Grote et al.

It is certified that error appears in the above-identified patent and that said Letters Patent is hereby corrected as shown below:

<u>Column 14,</u>
Line 2, delete "daimed in claim 1, wherein a 2-halo-6-methylbenzoic acid" and substitute -- claimed in claim 1, wherein a 2-halo-6-methylbenzoic acid --.

Signed and Sealed this

Twenty-third Day of May, 2006

JON W. DUDAS
*Director of the United States Patent and Trademark Office*